US008836343B2

(12) United States Patent
Tarui

(10) Patent No.: US 8,836,343 B2

(45) Date of Patent: Sep. 16, 2014

(54) FUEL PROPERTY DETECTION DEVICE AND METHOD FOR DETERMINING DETECTION OF PROPERTY OF FUEL

(75) Inventor: Jun Tarui, Kariya (JP)

(73) Assignee: Denso Corporation, Kariya (JP)

( * ) Notice: Subject to any disclaimer, the term of this patent is extended or adjusted under 35 U.S.C. 154(b) by 328 days.

(21) Appl. No.: 13/524,125

(22) Filed: Jun. 15, 2012

(65) Prior Publication Data

US 2013/0063155 A1 Mar. 14, 2013

(30) Foreign Application Priority Data

Sep. 10, 2011 (JP) ................................ 2011-197749

(51) Int. Cl.

*G01R 35/00* (2006.01)

*G01N 27/22* (2006.01)

(52) U.S. Cl.

CPC ................ *G01R 35/00* (2013.01); *G01N 27/22* (2013.01)

USPC ............................ 324/601; 324/663; 324/686

(58) Field of Classification Search

CPC ..... G01R 27/2605; G01D 5/24; G01D 5/2405

USPC ........... 73/1.02, 114.38, 304 C; 324/658–690

See application file for complete search history.

(56) References Cited

U.S. PATENT DOCUMENTS 7,030,629 B1 4/2006 Stahlmann et al.

2011/0029287 A1 * 2/2011 Sohn et al. .................... 702/189

FOREIGN PATENT DOCUMENTS

EP 1318376 A2 * 6/2003

* cited by examiner

*Primary Examiner* — Melissa Koval

*Assistant Examiner* — Daniel Miller

(57) ABSTRACT

First, second, and third electrodes are exposed to a fuel passage. The third electrode defines a first gap with the first electrode and defines a second gap with the second electrode. A property detection unit detects a property of fuel according to a summation of a first capacitance of the first gap and a second capacitance of the second gap. A correct-erroneous determination unit determines whether the property detected with the property detection unit is correct or erroneous according to a ratio of the summation and the first capacitance.

8 Claims, 5 Drawing Sheets

START

NORMAL MODE

S101 CONNECT WITH THIRD ELECTRODE GROUND FIRST AND SECOND ELECTRODES

S102 MEASURE SUMMATION OF C1 AND C2 AS ΣC

S103 COMPUTE Pc CORRESPONDING TO ΣC

S104 TEMPERATURE-CORRECT Pc

FAILSAFE MODE

S105 CONNECT WITH FIRST ELECTRODE GROUND THIRD AND SECOND ELECTRODES

S106 MEASURE C1

S107 COMPUTE RATIO BETWEEN ΣC and C1 as Rc

S108 Rc=Rcn? YES / NO

S109 CORRECT DETERMINATION

S110 SEND Pc

S111 ERRONEOUS DETERMINATION

S112 ERASE Pc

END

CONTROLLER
2
40
42
1
10
12
20
22
26
28
30
31
32
33
34
35
36
37
38
100
120
200
330
350
351
352
353

FUEL PROPERTY DETECTION DEVICE AND METHOD FOR DETERMINING DETECTION OF PROPERTY OF FUEL

CROSS REFERENCE TO RELATED APPLICATION

This application is based on reference Japanese Patent Application No. 2011-197749 filed on Sep. 10, 2011, the disclosure of which is incorporated herein by reference.

TECHNICAL FIELD

The present disclosure relates to a fuel property detection device configured to detect a property of fuel flowing through a fuel passage. The present disclosure further relates to a method for determining detection of property of fuel.

BACKGROUND

A conventional and known fuel property detection device is configured to measure a capacitance of a gap between electrodes exposed to a fuel passage and to detect the property of fuel according to the measurement result.

For example, a fuel property detection device of U.S. Pat. No. 7,030,629 includes a fuel pipe, which forms a first electrode and has a fuel passage extending therethrough, and a second electrode inserted in the fuel pipe. This configuration of U.S. Pat. No. 7,030,629 defines a gap between the first and second electrodes exposed to the fuel passage, and the gap receives fuel flowing though the fuel passage. This configuration of U.S. Pat. No. 7,030,629 enables to detect the property of fuel according to a capacitance of the gap between the first and second electrodes, since the capacitance changes correspondingly to the property of fuel flowing into the gap.

In order to enhance the accuracy of the property detection based on the capacitance of the gap between the electrodes, it is conceivable to reduce the distance between the electrodes as much as possible to enhance sensitivity relative to change in the capacitance. Nevertheless, in the fuel property detection device of U.S. Pat. No. 7,030,629, when the distance between the first and second electrodes is reduced, fuel, which has been measured of its property, easily retains in the gap between the electrodes. Consequently, the fuel is hardly replaced with undetected fuel with the property being changed. Thus, fuel stack occurs to cause erroneous detection of the fuel property before being changed. Even though, it is noted that the fuel property detection device of U.S. Pat. No. 7,030,629 does not have a fail-safe function to address such erroneous detection.

SUMMARY

It is an object of the present disclosure to produce a fuel property detection device having a fail-safe function with respect to erroneous detection. It is another object of the present disclosure to produce a method for determining detection of property of fuel.

According to an aspect of the present disclosure, a fuel property detection device configured to detect a property of fuel flowing through a fuel passage, the fuel property detection device comprises a first electrode exposed to the fuel passage. The fuel property detection device further comprises a second electrode exposed to the fuel passage. The fuel property detection device further comprises a third electrode exposed to the fuel passage, the third electrode defining a first gap with the first electrode and defining a second gap with the second electrode. The fuel property detection device further comprises a property detection unit configured to detect the property of fuel according to a summation of a first capacitance of the first gap and a second capacitance of the second gap. The fuel property detection device further comprises a correct-erroneous determination unit configured to determine whether the property detected with the property detection unit is correct or erroneous according to a ratio between the summation and the first capacitance.

According to another aspect of the present disclosure, a method for determining detection of a property of fuel flowing through a fuel passage, to which a first electrode, a second electrode, and a third electrode are exposed, the method comprises detecting the property of fuel according to a summation of a first capacitance of a first gap, which is defined between the third electrode and the first electrode, and a second capacitance of a second gap, which is defined between the third electrode and the second electrode. The method further comprises determining whether the detected property is correct or erroneous, according to a ratio between the summation and the first capacitance.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION

Figure 1:
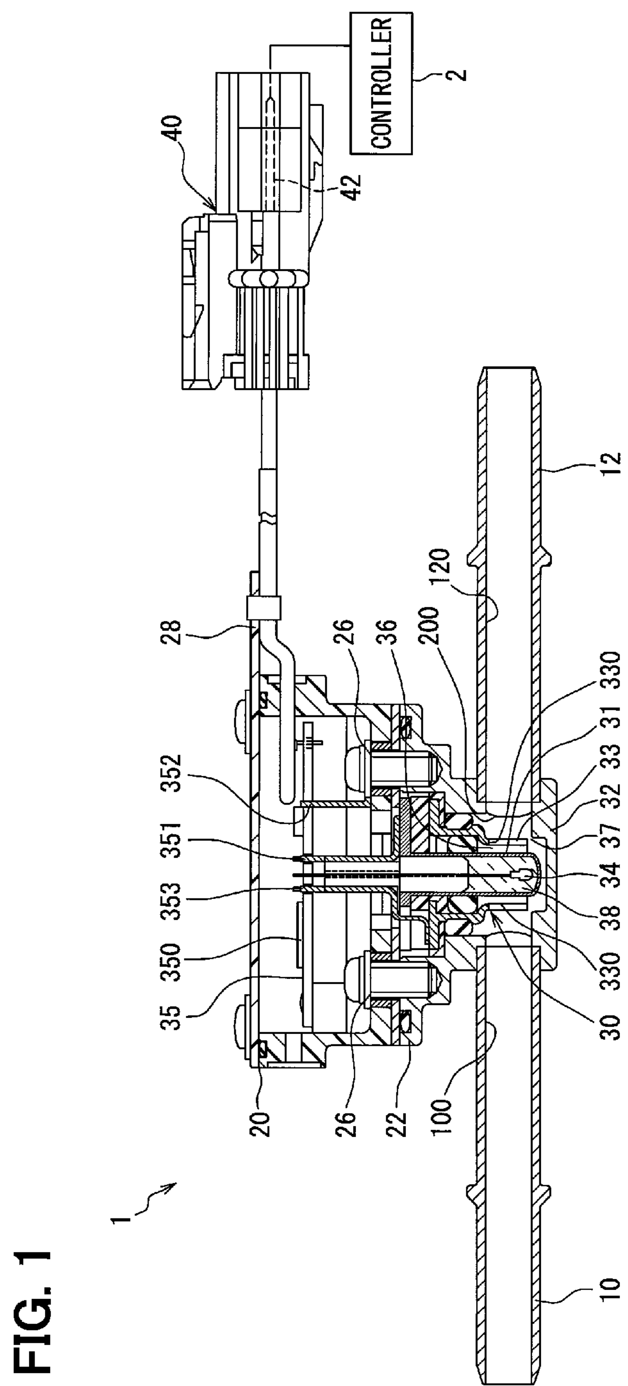
FIG. 1 is a sectional view showing a mechanical configuration of a fuel property detection device according to an embodiment of the present disclosure.
Figure 2:
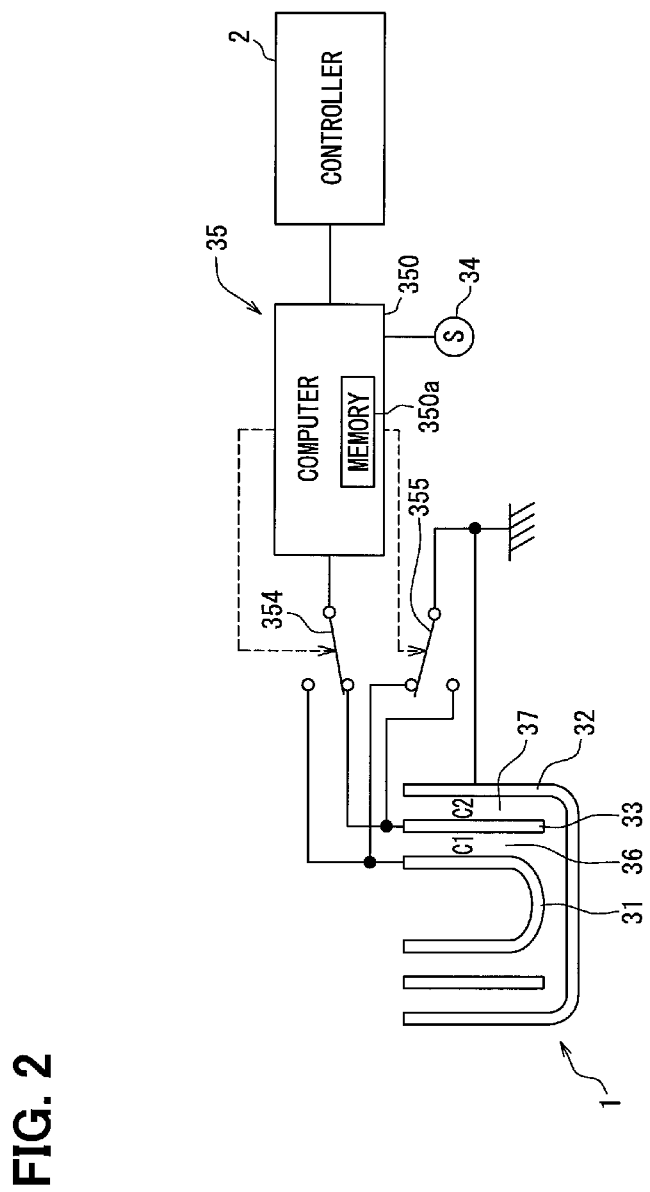
FIG. 2 is a block diagram showing an electrical configuration of the fuel property detection device according to the embodiment of the present disclosure.
Figure 3:
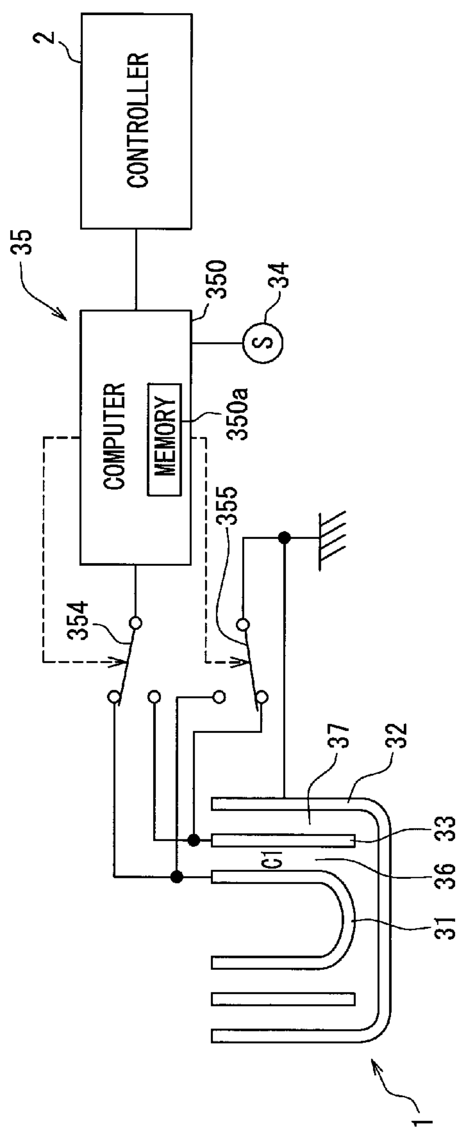
FIG. 3 is a block diagram showing an operation state different from that in FIG. 2.

As follows, an embodiment of the present disclosure will be described with reference to drawings. FIGS. 1 to 3 show a fuel property detection device 1 according to the embodiment of the present disclosure. The device 1 is equipped in an intermediate portion of a fuel supply passage, which is for supplying fuel from a fuel tank of a vehicle to a fuel injection valve of an internal combustion engine of the vehicle. The device 1 is configured to detect a property of fuel supplied through the fuel supply passage. The internal combustion engine is, for example, a gasoline engine configured to burn composite fuel being a mixture of gasoline and alcohol. The device 1 is configured to detect alcohol concentration as the property of fuel.

(Mechanical Configuration)

First, the mechanical configuration of the device 1 will be described as follows. As shown in FIG. 1, the device 1 includes an upstream fuel pipe 10, a downstream fuel pipe 12, an upper housing 20, a lower housing 22, a detection unit 30, an output unit 40, and the like.

The upstream fuel pipe 10 is connected to a portion of the fuel supply passage on the side of the fuel tank. The upstream fuel pipe 10 is in a tubular shape through which a fuel passage

100 extends. The downstream fuel pipe 12 is connected to a portion of the fuel supply passage on the side of the fuel injection valve. The downstream fuel pipe 12 is in a tubular shape through which a fuel passage 120 extends. The fuel pipes 10 and 12 are coaxial with each other and located at both sides of the lower housing 22.

The upper housing 20 is formed of resin and is in a hollow shape. The lower housing 22 is formed of metal and is in a hollow shape. The lower housing 22 is affixed to the upper housing 20. More specifically, the lower housing 22 is, for example, screwed to the upper housing 20 with multiple conductive screws 26. The lower housing 22 is fitted to both the fuel pipes 10 and 12. A fuel passage 200 extends through the lower housing 22 and communicates with the pipes 10 and 12. In the present configuration, the fuel passage 200 formed in the lower housing 22 is configured to flow fuel, which flows from the fuel tank through the fuel passage 100 of the upstream fuel pipe 10, to the downstream fuel pipe 12. The detection unit 30 is configured to detect the property of the fuel, which is flowing through the fuel passage 200 and to be supplied from the passage 200 to the fuel injection valve through the fuel passage 120 in the downstream fuel pipe 12.

The detection unit 30 includes a first electrode 31, a second electrode 32, a third electrode 33, a temperature sensor 34, a detection circuit 35, and the like. The first and third electrodes 31 and 33 are formed of metal and are coaxial with each other to have a double tubular configuration. The first and third electrodes 31 and 33 are inserted in the fuel passage 200 of the lower housing 22. The third electrode 33 surrounds the outer periphery of the first electrode 31. The third electrode 33 has a pair of fuel holes 330 extending therethrough and being coaxial with the fuel pipes 10 and 12. With the present configuration, the first and third electrodes 31 and 33 define a first gap 36 therebetween. The first gap 36 is configured to receive fuel flowing in the fuel passage 200 through the fuel hole 330. The second electrode 32 is formed in a lowermost portion of the metallic lower housing 22 and is opposed to one end of the third electrode 33 in the axial direction. With the present configuration, the second and third electrodes 32 and 33 define a second gap 37 therebetween. The second gap 37 is configured to receive fuel flowing in the fuel passage 200.

The temperature sensor 34 is, for example, a thermistor and is accommodated in the first electrode 31 together with a silicone-sealing member 38 being high in thermal conductivity. The temperature sensor 34 receives heat of fuel, which flows in the first gap 36, through the first electrode 31 and the silicone sealing member 38 thereby to measure temperature of the fuel.

The detection circuit 35 is mainly configured with a microcomputer (control computer) 350 accommodated in the upper housing 20. The detection circuit 35 is connected with the first and third electrodes 31 and 33 through terminals 351 and 353, respectively. The detection circuit 35 is further connected with the lower housing 22 including the second electrode 32 through the conductive screws 26 and a terminal 352. With the present configuration, the detection circuit 35 is enabled to detect an alcohol concentration as the fuel property, according to both a capacitance of the first gap 36 between the first and third electrodes 31 and 33 and a capacitance of the second gap 37 between the second and third electrodes 32 and 33. In addition, the detection circuit 35 is directly connected with the temperature sensor 34 and is configured to correct the detection result of the alcohol concentration according to the measurement result of the fuel temperature obtained with the sensor 34.

The output unit 40 is held with a cover portion 28 of the upper housing 20. The output unit 40 includes multiple kinds of terminals 42 for connecting the detection circuit 35 with a control circuit (engine control circuit) 2 of the internal combustion engine. With the present configuration, the detection circuit 35 is enabled to output detection information, which includes the detection result of the alcohol concentration corrected with the detected temperature, to the engine control circuit 2 through the terminals 42. The engine control circuit 2 is configured to compute an optimal air-fuel ratio of the internal combustion engine, according to the detection result of the alcohol concentration included in the detection information received from the detection circuit 35. The engine control circuit 2 is further configured to compute an injection quantity of fuel from the fuel injection valve, according to the computation result of the optimal air-fuel ratio.

(Electrical Configuration)

Subsequently, the electrical configuration of the device 1 will be described as follows. As shown in FIGS. 2 and 3, the second electrode 32 is regularly grounded through the fuel pipes 10 and 12 outside the lower housing 22 and the grounding terminal 42 (FIG. 1) and the detection circuit 35 of the device 1.

The detection circuit 35 is equipped with switch devices 354 and 355 each configured with, for example, a semiconductor switching element. As shown in FIGS. 2 and 3, one switch device 354 is configured to switch between the first and third electrodes 31 and 33 to be electrically connected as a detection terminal with a control computer 350. As shown in FIGS. 2 and 3, the other switch device 355 is configured to switch between the first and third electrodes 31 and 33 to be grounded. The control computer 350 controls the switch devices 354 and 355 to implement the switching operations of the electrodes.

The detection circuit 35 is further configured to cause the control computer 350 to measure the capacitances C1 and C2 of the first and second gaps 36 and 37 according to an electric output from one of the electrodes 31 to 33 electrically connected with the control computer 350 for detecting the fuel property. Although, not shown in FIGS. 2 and 3, various configurations may be employable for measuring the capacitances C1 and C2. For example, an oscillating circuit configured to cause oscillation with the capacitances C1 and C2 may be employable for measuring the capacitances C1 and C2. The detection circuit 35 is further configured to cause the control computer 350, which is electrically connected with the temperature sensor 34, to implement temperature correction of the alcohol concentration.

(Operation and Effect)

Figure 4:
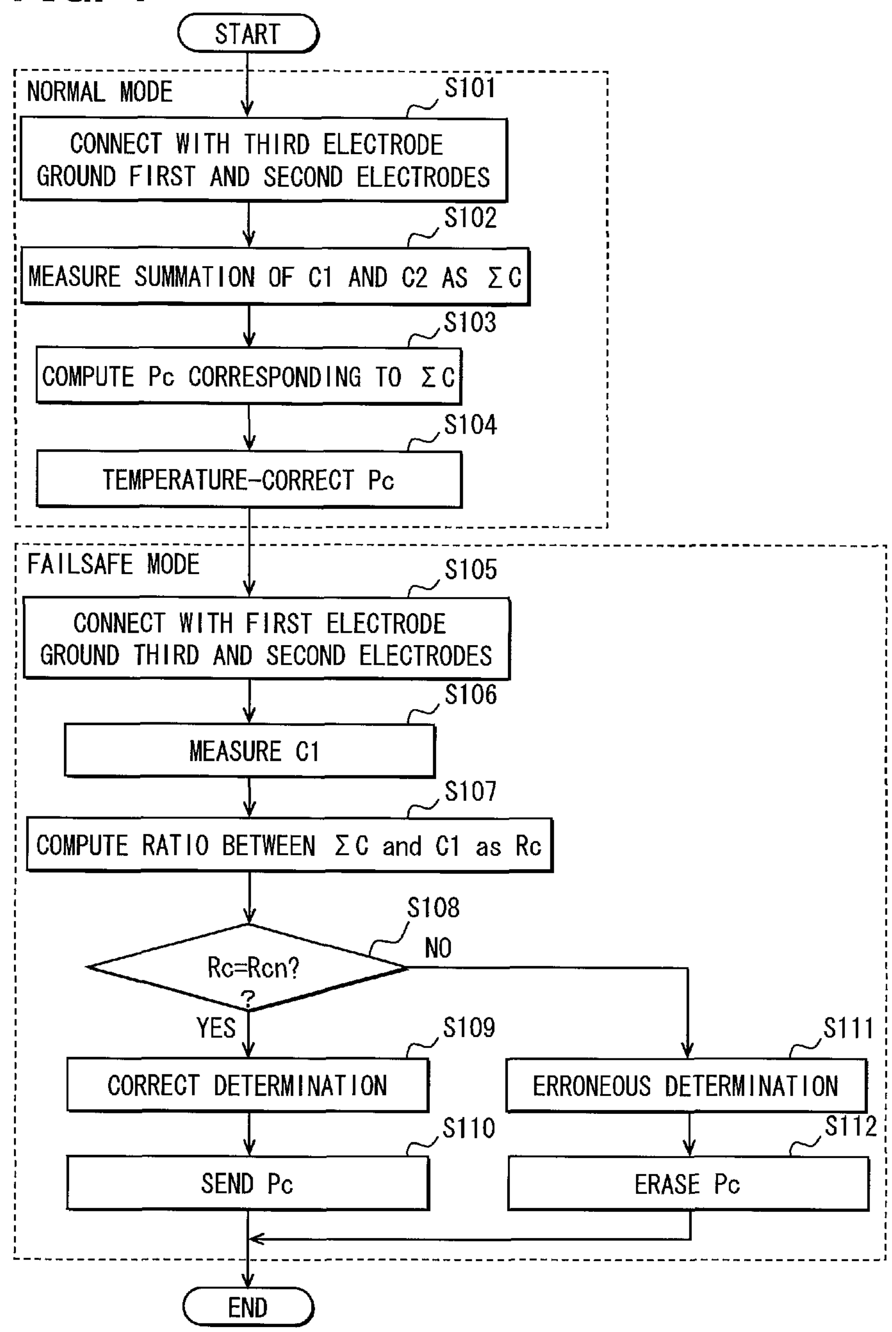
FIG. 4 is a flowchart showing a detection procedure of the fuel property detection device according to the embodiment of the present disclosure.

Subsequently, the operation and the effect of the device 1 will be described as follows. In the detection circuit 35, the control computer 350 is configured to execute a computer program stored in a memory 350*a* (FIGS. 2 and 3) thereby to execute a detection flow shown in FIG. 4.

First, the control computer 350 implements an operation of S101 to S104 in a normal mode, in response to a detection command from the engine control circuit 2. Specifically, at S101, as shown in FIG. 2, the control computer 350 controls the switch device 354 to connect the control computer 350 electrically with the third electrode 33 and controls the switch device 355 to ground the first electrode 31 in addition to the second electrode 32. In this way, the control computer 350 selects, as electrodes for property detection, the first and second electrodes 31 and 32, each being at the grounding potential, and the third electrode 33, which generates an electric output corresponding to the capacitances C1 and C2 with the electrodes 31 and 32, respectively. Subsequently, at S102, the control computer 350 measures, as a total capacitance ΣC, a summation of the capacitance C1 of the first gap 36 and the capacitance C2 of the second gap 37 based on the electric output from the third electrode 33 relative to the first and second electrodes 31 and 32 each being at the grounding potential.

Figure 5A:
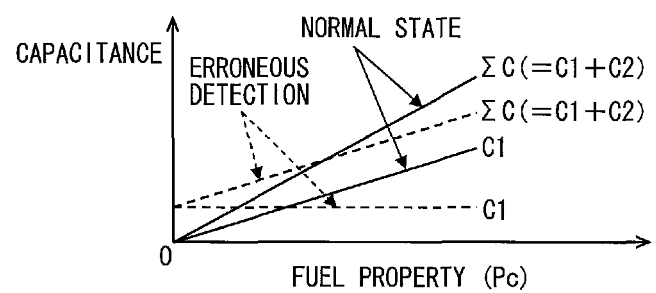
FIG. 5A and FIG. 5B are graphs each showing a characteristic of the fuel property detection device according to the embodiment of the present disclosure.

Subsequently, at S103, the control computer 350 computes an alcohol concentration Pc corresponding to the total capacitance ΣC measured at S102. As shown by the solid line in the graph of FIG. 5A, the total capacitance ΣC has a correlation with the alcohol concentration Pc. Therefore, the control computer 350 can compute the alcohol concentration Pc based on the correlation, which is stored as a correspondence, a data map, or the like, in the memory 350*a* and the measurement result of the total capacitance ΣC. At subsequent S104, the control computer 350 corrects the alcohol concentration Pc, which is computed at S103, with the measurement result of the fuel temperature obtained from the temperature sensor 34.

Thus, the control computer 350 terminates the normal mode as described above, without sending, as a detection result of the fuel property, the alcohol concentration Pc with temperature correction to the engine control circuit 2. In the following description, the alcohol concentration Pc with temperature correction is simply referred to as the alcohol concentration Pc. Thus, the control computer 350 changes the normal mode to the failsafe mode of S105 to S112. Specifically, at S105, as shown in FIG. 3, the control computer 350 controls the switch device 354 to connect the control computer 350 electrically with the first electrode 31 and controls the switch device 355 to ground the third electrode 33 in addition to the second electrode 32. In this way, the control computer 350 selects, as electrodes for property detection, the third electrode 33 and the first electrode 31. The third electrode 33 is at the grounding potential and has the capacitance C2, which is substantially zero with the second electrode 32 at the same electric potential. The first electrode 31 generates an electric output corresponding to the first capacitance C1 with the third electrode 33. Subsequently, at S106, the control computer measures the first capacitance C1 of the first gap 36 from the electric output of the first electrode 31 relative to the third electrode 33 at the grounding potential.

Figure 5B:
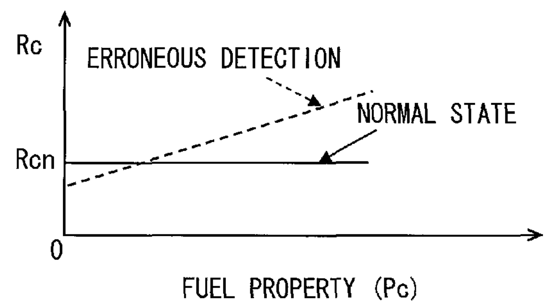

Subsequently, at S107, the control computer 350 computes the ratio Rc between the total capacitance ΣC measured at S102 and the first capacitance C1 measured at S106. When fuel having the same property flows into the gaps 36 and 37, as shown by the solid line in the graph of FIG. 5B, the ratio Rc, which is between the total capacitance ΣC of both the gaps 36 and 37 and the first capacitance C1 of only the first gap 36, is at a constant normal value Rcn relative to an arbitrary alcohol concentration Pc. This is because, as shown by the solid lines in the graph of FIG. 5A, the correlation exists between the first and second capacitances C1 and C2 and the alcohol concentration Pc, which is the fuel property. To the contrary, when the property of fuel flowing into the first gap 36 is different from the property of fuel flowing into the second gap 37, the first and second capacitances C1 and C2 occur in correlation with the properties. Therefore, as shown by the dashed line in the graph of FIG. 5B, the ratio Rc between the total capacitance ΣC and the first capacitance C1 is shifted from the normal value Rcn. In consideration of these facts, even when fuel is retained in either of the gaps 36 and 37, erroneous detection resulting from difference in property of fuel in the gaps 36 and 37 can be determined correctly, according to comparison between the ratio Rc, which is between the total capacitance ΣC and the first capacitance C1, and the normal value Rcn.

Therefore, at S108, the control computer 350 compares the ratio Rc, which is between the total capacitance ΣC and the first capacitance C1, with the normal value Rcn stored in the memory 350*a* of the control computer 350. The control computer 350 further determines whether the ratio Rc substantially coincides with the normal value Rcn such that the difference therebetween is within a predetermined error range. When the ratio Rc substantially coincides with the normal value Rcn with the difference within the error range, at S109, the control computer 350 makes determination of a normal detection that the alcohol concentration Pc detected at S101 to S104 is correct. In this case, at subsequent S110, the control computer 350 sends the alcohol concentration Pc to the engine control circuit 2. With the present configuration, the engine control circuit 2 is enabled to determine the fuel injection quantity according to the alcohol concentration Pc detected correctly. It is noted that, the alcohol concentration Pc is detected with high accuracy according to the total capacitance ΣC, which is greater in change width than one of the capacitances C1 and C2. Therefore, the fuel injection quantity can also be determined with high accuracy.

To the contrary, when the difference between the ratio Rc and the normal value Rcn is greater than the error range, the ratio Rc does not coincide with the normal value Rcn. In this case, at S111, the control computer 350 makes determination of an erroneous detection that the alcohol concentration Pc detected at S101 to S104 has an error. In this case, at subsequent S112, the control computer 350 erases the alcohol concentration Pc measured at S101 to S104, without sending the alcohol concentration Pc to the engine control circuit 2. In this way, the engine control circuit 2 is restricted from determining the fuel injection quantity according to the alcohol concentration Pc with error. As described above, according to the present embodiment, even if fuel retains in either of the gaps 36 and 37 to cause fuel stack and to cause erroneous detection, it is possible to avoid erroneous determination of the fuel injection quantity based on the alcohol concentration Pc with error obtained from the erroneous detection. Thus, high fail-safe function can be produced.

Additionally, in the normal mode of S101 to S104, the entire gaps 36 and 37 defined between the third electrode 33 and the first and second electrodes 31 and 32 at the grounding potential cause the change in the total capacitance ΣC according to the alcohol concentration Pc of fuel in each of the gaps 36 and 37. Therefore, in the normal mode, in which the first and second electrodes 31 and 32 are selected as the grounded electrodes, and in which the third electrode 33 is selected as the electrically connected electrode, the total capacitance ΣC reflecting the alcohol concentration Pc in each of the gaps 36 and 37 can be measured with high accuracy. In addition, in the failsafe mode at S105 to S112, the second capacitance C2 of the second gap 37, which is between the second and third electrodes 32 and 33 at the grounding potential, is substantially zero. With the present configuration, change in the first capacitance C1 occurs correspondingly to the alcohol concentration Pc of fuel in the first gap 36, which is between the third electrode 33 at the grounding potential and the first electrode 31, regardless of the second electrode 32. Therefore, in the failsafe mode, in which the first electrode 31 is selected as the electrically connected electrode, and in which the second and third electrodes 32 and 33 are selected as the grounded electrodes, the first capacitance C1 reflecting the alcohol concentration Pc in the first gap 36 can be measured with high accuracy. Therefore, the erroneous detection determination can be implemented with high accuracy based on the precise measurement result.

In addition, the lower housing 22 having the fuel passage 200 extending therethrough is grounded externally. Therefore, the second electrode 32 exposed to the fuel passage 200 can be grounded in both the normal mode and the failsafe mode with a simple configuration. In addition, the first and third electrodes 31 and 33 are inserted into the lower housing 22. Therefore, the electrodes 31 and 33 can be exposed in the fuel passage 200 with a simple configuration. In view of the above facts, accuracy of the erroneous detection determination can also be enhanced with the simple configuration.

In the above described embodiment, the control computer 350 configured to implement S103 and S104 of the detection flow is equivalent to a property detection unit. In addition, the control computer 350 configured to implement S107 to S112 of the detection flow is equivalent to a correct-erroneous determination unit. Furthermore, both the control computer 350 configured to implement S101, S102, S105, and S106 of the detection flow and the switch devices 354 and 355 are equivalent to a mode switch unit.

Other Embodiment

As described above, the present disclosure is not limited to the above embodiment, and is capable of being applied to various embodiments as long as being undeviating from the gist thereof.

Specifically, the detection circuit 35 may have a modified electrical configuration to electrically connect both the first and second electrodes 31 and 32 with the control computer 350 and to ground the third electrode 33 at S101 in the normal mode. In addition, the detection circuit 35 may have a modified electrical configuration to ground the first electrode 31 and to electrically connect both the second and third electrodes 32 and 33 with the control computer 350 at S105 in the failsafe mode. In addition, the implementation order of at least S101 and S102 in S101 to S104 in the normal mode may be exchanged with S105 and S106 in the failsafe mode. The temperature sensor 34 may be omitted from the detection unit 30. In this case, S104 in the normal mode may be omitted. In addition, the correspondence between the electrodes 31 to 33 and the first to third electrodes may be arbitrarily modified in the mechanical configuration. In addition, the electrical configuration and the detection flow may be modified correspondingly to the modification of the correspondence.

The above-described fuel property detection device is configured to detect the property of fuel flowing through the fuel passage. The fuel property detection device includes: the first and second electrodes exposed to the fuel passage; the third electrode exposed to the fuel passage, the third electrode defining with the first electrode a first gap configured to receive fuel to be detected, and the third electrode defining with the second electrode a second gap configured to receive fuel to be detected; the property detection unit configured to detect the property of fuel to be detected according to the summation of the first capacitance of the first gap and the second capacitance of the second gap; and the correct-erroneous determination unit configured to determine whether the property detected with the property detection unit is correct or erroneous according to the ratio of the summation and the first capacitance.

According to the configuration of the present disclosure, fuel passing through the fuel passage, to which all the electrodes are exposed, flows into the first gap between the first and third electrodes and the second gap between the second and third electrodes. With the present configuration, the summation of the first capacitance of the first gap and the second capacitance of the second gap is greater than the capacitance of each electrode in change relative to change in the property of fuel flowing in each gap. Therefore, the property of fuel can be detected with high accuracy based on the summation.

Further, as long as fuel of the same property flows into the first and second gaps, the ratio of the summation of the first and second capacitances, which is the capacitance of the entire gaps, and the first capacitance of only the first gap is a constant normal value with respect to an arbitrary property. This relationship is formed, since the first and second capacitances have a correlation, such as a proportional relation, therebetween. To the contrary, when the property of fuel flowing into the first gap is different from the property of fuel flowing into the second gap, the first and second capacitances differ from each other correspondingly to the property of fuel. Consequently, the ratio of the summation of the capacitances and the first capacitance is shifted from the normal value. In consideration of this, even if fuel retains in either of the first and second gaps, erroneous detection, which results from the difference in properties in the gaps, can be determined according to the ratio of the summation of the capacitances and the first capacitance. Therefore, the fail-safe function can be produced with respect to the erroneous detection resulting from fuel stack.

The correct-erroneous determination unit may be further configured to compare the ratio of the summation of the first and second capacitances and the first capacitance with the normal value. In this case, the correct-erroneous determination unit may be further configured to determine that the property detected with the property detection unit is erroneous when the result of the comparison represents that the ratio of the summation and the first capacitance doses not coincide with the normal value.

With the present configuration, even when fuel retains in either of the first and second gaps, the ratio of the summation of the first and second capacitances and the first capacitance does not coincide with the normal value being compared. Therefore, the determination that the result of the property detection is erroneous, i.e., determination of erroneous detection, can be made correctly. Therefore, the fail-safe function can be produced correctly with respect to the erroneous detection resulting from fuel stack.

The fuel property detection device may further include the mode switch unit configured to switch between the normal mode, which is to select the first to the third electrodes and to measure the summation of the first and second capacitances, and the failsafe mode, which is to select the first electrode and the third electrode and to measure the first capacitance. The mode switch unit may be further configured to implement the switched one of the normal mode and the failsafe mode. In this case, the property detection unit may be further configured to implement the property detection according to the summation measured in the normal mode. In addition, the correct-erroneous determination unit may be further configured to implement the correct-erroneous determination according to the ratio of the summation and the first capacitance measured in the normal mode and the failsafe mode.

The present configuration switches the normal mode, which is needed to select the first to third electrodes to measure the summation of the first and second capacitances, and the failsafe mode needed to select the first and third electrodes to measure the first capacitance. Thus, in the failsafe mode, only the first capacitance can be measured correctly, regardless of the second electrode generating the second capacitance. Therefore, the erroneous detection resulting from fuel stack can be determined correctly according to the first capacitance in the failsafe mode.

The mode switch unit may be further configured to electrically connect with the third electrode and to ground the first and second electrodes in the normal mode. In this case, the mode switch unit may be further configured to electrically connect with the first electrode and to ground the second and third electrodes in the file safe mode.

In the normal mode, the first and second electrode at the grounding potential and the third electrode form the first and second gaps thereamong. Further, fuel flowing into the first and second gaps causes change in the summation of the first and second capacitances correspondingly to the change in the property of fuel. Therefore, in the normal mode, in which the first and second electrodes are selected as the grounded electrodes, and in which the third electrode is selected as the electrically connected electrode, the total capacitance of the first and second capacitances reflecting the fuel property in each of the gaps can be measured with high accuracy. To the contrary, in the failsafe mode, the second capacitance of the second gap between the second and third electrodes at the grounding potential is substantially zero. Therefore, change arises in the first capacitance of the first gap between the third electrode at the grounding potential and the first electrode correspondingly to the property fuel flowing thereinto. Therefore, in the failsafe mode, in which the first electrode is selected as the electrically connected electrode, and in which the second and third electrodes are selected as the grounded electrodes, the first capacitance reflecting the fuel property in the first gap can be measured with high accuracy. Therefore, the erroneous detection determination can be implemented with high accuracy based on the precise measurement result.

The second electrode may be formed with the housing grounded externally, the housing having the fuel passage extending therethrough. In this case, the first and third electrodes may be inserted in the housing.

With the present configuration, the housing having the fuel passage extending therethrough is grounded externally, and therefore, the second electrode exposed to the fuel passage can be grounded in both the normal mode and the failsafe mode with the simple configuration. In addition, the first and third electrodes are inserted into the housing. Therefore, the electrodes can be exposed in the fuel passage with the simple configuration. In view of the above facts, accuracy of the erroneous detection determination can also be enhanced with the simple configuration.

The property detection unit may be further configured to erase the result of property detection when the correct-erroneous determination unit makes the determination that the result of property detection is erroneous.

With the present configuration, even when fuel retains in either of the first and second gaps, the property detection result is erased in the case where determination of erroneous detection that the property detection result is erroneous is made. Therefore, high fail-safe function can be produced with respect to the erroneous detection.

The above processings such as calculations and determinations are not limited being executed by the control computer 350. The control configuration may have various structures including the control computer 350 shown as an example.

The above processings such as calculations and determinations may be performed by any one or any combinations of software, an electric circuit, a mechanical device, and the like. The software may be stored in a storage medium, and may be transmitted via a transmission device such as a network device. The electric circuit may be an integrated circuit, and may be a discrete circuit such as a hardware logic configured with electric or electronic elements or the like. The elements producing the above processings may be discrete elements and may be partially or entirely integrated.

It should be appreciated that while the processes of the embodiments of the present disclosure have been described herein as including a specific sequence of steps, further alternative embodiments including various other sequences of these steps and/or additional steps not disclosed herein are intended to be within the steps of the present disclosure.

While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A fuel property detection device configured to detect a property of fuel flowing through a fuel passage, the fuel property detection device comprising:

a first electrode exposed to the fuel passage;

a second electrode exposed to the fuel passage;

a third electrode exposed to the fuel passage, the third electrode defining a first gap with the first electrode and defining a second gap with the second electrode;

a property detection unit configured to detect the property of fuel according to a summation of a first capacitance of the first gap and a second capacitance of the second gap; and a correct-erroneous determination unit configured to determine whether the property detected with the property detection unit is correct or erroneous according to a ratio between the summation and the first capacitance.

2. The fuel property detection device according to claim 1, wherein the correct-erroneous determination unit is further configured to compare the ratio between the summation and the first capacitance with a normal ratio value and to determine that the property detected with the property detection unit is erroneous when the comparison represents that the ratio between the summation and the first capacitance does not coincide with the normal ratio value.

3. The fuel property detection device according to claim 1, further comprising:

a mode switch unit configured to implement selectively one of a normal mode to select the first, second and third electrodes and to measure the summation and a failsafe mode to select the first electrode and the third electrode and to measure the first capacitance, wherein the property detection unit is further configured to detect the property according to the summation measured in the normal mode, and the correct-erroneous determination unit is further configured to determine whether the property detected with the property detection unit is correct or erroneous according to the ratio between the summation and the first capacitance measured in the normal mode and the failsafe mode.

4. The fuel property detection device according to claim 3, wherein the mode switch unit is further configured, in the normal mode, to electrically connect with the third electrode and to ground the first and second electrodes, and the mode switch unit is further configured, in the failsafe mode, to electrically connect with the first electrode and to ground the second and third electrodes.

5. The fuel property detection device according to claim 4, wherein the second electrode is formed with a housing grounded externally, the housing having the fuel passage extending therethrough, and the first and third electrodes are inserted in the housing.

6. The fuel property detection device according to claim 1, wherein the property detection unit is further configured to erase a result of detection of the property when the correct-erroneous determination unit makes a determination that the result is erroneous.

7. A method for determining detection of a property of fuel flowing through a fuel passage, to which a first electrode, a second electrode, and a third electrode are exposed, the method comprising:

detecting, using a property detection unit, the property of fuel according to a summation of a first capacitance of a first gap, which is defined between the third electrode and the first electrode, and a second capacitance of a second gap, which is defined between the third electrode and the second electrode; and determining, using a correct-erroneous determination unit, whether the detected property is correct or erroneous according to a ratio between the summation and the first capacitance.

8. A non-transitory computer readable medium comprising instructions executed by a computer, the instructions including the method according to claim 7.

* * * * *